United States Patent [19]

Nagato et al.

[11] 4,130,577
[45] Dec. 19, 1978

[54] PROCESS FOR PREPARING α,α-DIMETHYLBENZYL ISOCYANATES

[75] Inventors: Nobuyuki Nagato, Wako; Taketoshi Naito, Yokohama, both of Japan

[73] Assignee: Showa Denko K.K., Tokyo, Japan

[21] Appl. No.: 844,815

[22] Filed: Oct. 25, 1977

[30] Foreign Application Priority Data

Oct. 25, 1976 [JP] Japan ................................. 51-127168

[51] Int. Cl.$^2$ .......................................... C07C 118/00
[52] U.S. Cl. ................................................ 260/453 P
[58] Field of Search ..................................... 260/453 P

[56] References Cited

U.S. PATENT DOCUMENTS

| 3,816,499 | 6/1974 | Beswick et al. ................... 260/453 P |
| 3,948,966 | 4/1976 | Inamoto et al. ................... 260/453 P |
| 4,056,547 | 11/1977 | Tanaka et al. ..................... 260/453 P |

Primary Examiner—Dolph H. Torrence
Attorney, Agent, or Firm—Wenderoth, Lind & Ponack

[57] ABSTRACT

Process for preparing α,α-dimethylbenzyl isocyanate or its derivatives which comprises reacting the corresponding organic halide in an anhydrous condition in the presence of a specified catalyst with an alkali metal cyanate in an aprotic solvent which forms no salt with a hydrogen halide.

9 Claims, No Drawings

PROCESS FOR PREPARING α, α-DIMETHYLBENZYL ISOCYANATES

This invention relates to a process for preparing α, α-dimethylbenzyl isocyanate or its derivatives of the formula

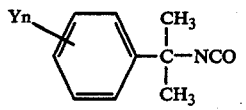

wherein Y is a halogen atom, or an alkyl, haloalkyl or alkoxy group each containing 1 to 4 carbon atoms, and n is 0, 1 or 2.

The organic isocyanates of the above formula are useful as intermediates for synthesis of various organic substances, especially of agricultural chemicals. For example, reaction of the organic isocyanates with primary or secondary amines yields urea derivatives which are useful as herbicides. One specific example of these agricultural chemicals is N-α, α-dimethylbenzyl-N'-methoxy-N'-phenylurea.

The most common synthetic route of organic isocyanates by the prior art techniques is based on the reaction of the corresponding organic amines with phosgene. However, phosgene is a very toxic substance, and is difficult to handle, and especially to transport safely. Moreover, every measure must be taken to prevent its leakage during storage and reaction operation. Accordingly, this method has the defect that the equipment for producing phosgene must be provided at a site which is adjacent the place of its use. The organic amine, the other starting material, is also difficult to produce. For example, even the reaction of α,α-dimethylbenzyl chloride with ammonia, which is considered to be most advantageous for producing α,α-dimethylbenzyl amine, requires elevated pressures, and the yield of the final product is not always high. Thus, the method has technical problems still to be solved.

Attempts were made to produce organic isocyanates by the reaction of organic halides with alkali metal cyanates. Such a method was considered commercially advantageous over the aforesaid method using phosgene because the organic halides, especially the chlorides, are relatively easily available and the alkali metal cyanates have very low toxicity as compared with phosgene and are easy to handle, and in particular sodium cyanate is commercially available at low cost. Actually, however, this reaction was not as simple as had been expected, and no satisfactory technique has been established up to date. This prior art technique is described hereinbelow in some detail.

It is generally known that the reactivity of an organic halide with an alkali metal cyanate is very poor, and mere mixing and heating of these materials do not induce reaction, and that the desired isocyanate can scarcely be obtained even when the reaction is carried out in nonpolar or weakly polar solvent such as water, ethers, alcohols, esters, ketones, nitriles, hydrocarbons, halogenated hydrocarbons and nitrated hydrocarbons (see, for example, U.S. Pat. No. 2,866,801). In order to overcome this difficulty, some suggestions have been made in the past. They include, for example, the method which comprises reacting a certain organic halide with an alkali metal cyanate in a strongly polar aprotic solvent such as dimethyl formamide (DMF), dimethyl sulfoxide (DMSO) or dimethyl sulfone (Japanese Patent Publication No. 4372/63 and U.S. Pat. Nos. 2,866,801 and 3,017,420) and the method which involves using a quaternary ammonium halide or a tertiary amine, such as tetraethylammonium iodide or trimethylamine, as a reaction catalyst (U.S. Pat. No. 2,866,802). All of these methods, however, have the defect that the resulting isocyanate undergoes trimerization to form a large quantity of an isocyanurate as a by-product. For example, reaction of benzyl chloride with sodium cyanate in dimethyl formamide for several minutes gives benzyl isocyanate, and simultaneously, a large quantity of tribenzyl isocyanurate is formed. If the reaction time is prolonged, the isocyanurate alone is obtained almost quantitatively (see the Examples of U.S. Pat. No. 2,866,801; and U.S. Pat. No. 3,037,979).

Moreover, the above methods are limited to those starting organic halides which have a primary or secondary alkyl halide group, i.e. organic halides having at least one hydrogen atom on the halogen-substituted carbon atom, and cannot be applied to those organic halides having a tertiary alkyl halide group, i.e. organic halides having no hydrogen atom on the halogen-substituted carbon atom. When an organic halide which has no hydrogen atom on the halogen-substituted carbon atom, but has a hydrogen atom on a carbon atom adjacent the aforesaid carbon atom, such as α,α-dimethylbenzyl halide, is heated in a strongly polar solvent such as dimethyl formamide or dimethyl sulfoxide, or is reacted in the presence of an amine as a catalyst, the organic halide readily undergoes intramolecular dehydrohalogenation to form an olefin, and the desired isocyanate cannot be obtained.

Some methods are shown below which were suggested in the past to produce organic isocyanates from organic halides having a tertiary alkyl halide group, such α,α-dimethylbenzyl halides, and alkali metal cyanates or other cyanates.

(a) An organic halide is reacted with an alkali metal cyanate in a medium consisting of water and a solvent miscible with the organic halide with the aid of an interphase transferable catalyst such as n-cetyltrimethylammonium bromide (Chem. Abst. Vol. 84, 1976, 30650 p). Based on the fact that the alkali metal cyanate, one of the reactants, is scarcely soluble in common organic solvents but well soluble in water, and the organic halide, the other reactant, is well soluble in organic solvents but is scarcely soluble in water, this method uses as an inter-phase transferable catalyst a salt which in the form of halogen salt, is soluble in water but difficultly soluble in organic solvents, and in the form of cyanic acid salt, has an increased solubility in the organic solvents, such as $R_4NX$, $R_4PX$, $R_4AsX$ or $MX_nY_m$ (where R=alkyl or aryl radical, M=metal, $Y=R_3P$, $R_3PO$ or $R_3N$, and X is chlorine or bromine in the case of the halogen salt, and OCN— in the case of the cyanic acid salt), and causes the reaction to proceed with the aid of this catalyst.

Hence, in order for the inter-phase transferable catalyst to function, the presence of water in the reaction system is essential. However, when the starting material is an α,α-dimethylbenzyl halide, the presence of water in the reaction system inevitable causes undesirable side reactions, such as the hydrolysis of the starting material to form a carbinol, the decomposition of the resulting isocyanate to form an amine, or the further reaction of the by-product amine with the isocyanate to form a disubstituted urea compound, and the intended isocyanate cannot be obtained in satisfactory yields.

(b) Another prior method comprises reacting the organic halide in an organic solvent with a cyanate soluble in the organic solvent, for example a quaternary ammonium salt, quaternary phosphonium salt, sulfonium salt, arsonium salt, large-ring heterocyclic compound complex or metal complex (Chem. Abst. Vol. 84, 1976, 30649 v). According to this method, cyanic acid salts soluble in organic solvents are used as reactants instead of the alkali metal cyanates which are insoluble in organic solvents. These soluble cyanic acid salts are the same substances as the cyanic acid salt form of the inter-phase transferable catalyst used in method (a) described above. In this regard, methods (a) and (b) basically have a common technical concept. The method (b) cannot use alkali metal cyanates available at low cost, and requires the production of the cyanic acid salts which are soluble in organic solvents. The production of these compounds is not simple, and requires separate manufacturing equipment. Moreover, the effluent from the process of producing the cyanic acid salts contains large quantities of phosphorus compounds, amines or heavy metals, and enormous amounts of labor and expenditure must go into the disposal of these unwanted inclusions.

It will be understood from the above description of the prior art that the production of organic isocyanates by the reaction of organic halides with cyanates, especially alkali metal cyanates, encounters difficulties, and the production of organic isocyanates by the reaction of organic halides having a tertiary alkyl halide group, such as an α,α-dimethylbenzyl halide, with alkali metal cyanates, involves various difficulties and problems. These difficulties are due mainly to the poor reactivity of the organic halides with the alkali metal cyanates and to the fact that the α,α-dimethylbenzyl halides are unstable substances and readily decompose by intramolecular dehydrohalogenation.

It has now been found that the present invention can overcome the difficulties of the prior art techniques. It is an object of this invention therefore to provide a commercially advantageous process for producing α,α-dimethylbenzyl isocyanate or its derivatives in high yields without difficulty from an α,α-dimethylbenzyl halide or its derivative and an alkali metal cyanate.

The present invention thus provides a process for preparing α,α-dimethylbenzyl isocyanate or its ring-substituted derivatives of the formula

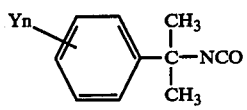

wherein Y is a halogen atom or an alkyl, haloalkyl or alkoxy group each having 1 to 4 carbon atoms and n is an integer of 0, 1 or 2,
which comprises reacting an α,α-dimethylbenzyl halide or its ring-substituted derivative of the formula

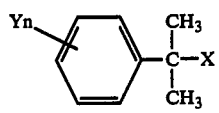

(1)

wherein X is chlorine or bromine, and Y and n are as defined above,
with an alkali metal cyanate in an organic solvent in a substantially anhydrous condition at a temperature of between 0° C. and 150° C. in the presence of, as a catalyst, at least one member selected from the group consisting of metallic V, Mn, Co, Zn, Pd and Sn and oxides and mineral acid salts or carboxylic acid salts of these metals, said organic solvent being an aprotic solvent which forms no salt or adduct with a hydrogen halide.

The above reaction can be schematically shown as follows:

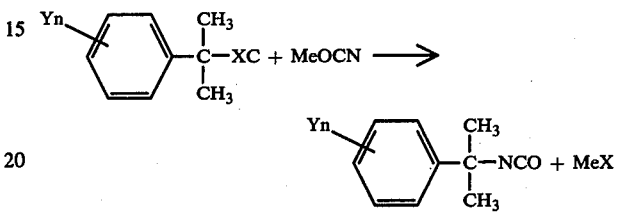

In the formula, Y, n and X are as defined above, and Me represents an alkali metal. A small amount of α-methylstyrene is formed as a by-product.

Preferred embodiments of the present invention are described in more detail below.

Typical examples of the starting organic halide of formula (1) are α,α-dimethylbenzyl chloride, α,α-dimethylbenzyl bromide, and ring-substituted derivatives of these compounds, for example those in which the benzene ring is substituted by an atom or group such as m-chloro, p-chloro, m-bromo, p-bromo, m-fluoro, p-fluoro, 3,4-dichloro, 2,4-dichloro, m-methyl, p-methyl, m-ethyl, p-ethyl, p-n-propyl, p-isopropyl, p-tert, butyl, 3,4-dimethyl, 3-methyl-4-chloro, 3-chloro-4-methyl, 3-fluoro-4-methyl, m-chloromethyl, p-trichloromethyl, m-chlorofluoromethyl, p-trifluoromethyl, p-2-chloro-iso-propyl, m-methoxy, p-methoxy, m-ethoxy, p-ethoxy, m-n-propoxy, or p-isopropoxy. The final product obtained is α,α-dimethylbenzyl isocyanate or its ring-substituted derivatives corresponding to these examples.

Sodium cyanate and potassium cyanate are preferred as the alkali metal cyanate, the other starting material.

The molar ratio of the starting compound of formula (1) to the alkali metal cyanate is not particularly restricted. Usually, it is 1:0.8 to 1:4, preferably 1:1 to 1:2. Generally, it is preferred to use the alkali metal cyanate somewhat in excess.

The catalyst used includes the aforesaid metals, and the oxides or the salts of these metals. Of these, the mineral acid salts or carboxylic acid salts of the metals are preferred. It is not essential that the catalyst as added to the reaction system be in a form soluble in the reaction system. Like the metals themselves or their oxides, the catalyst may be initially insoluble in the reaction system. Preferred examples of the mineral acid salts or carboxylic acid salts are the chlorides, bromides, sulfates, nitrates, formates, acetates, propionates, butyrates, and naphthenates which are all available at low cost.

The amount of the catalyst is not particularly restricted, but if it is too small, a sufficient effect cannot be obtained. On the other hand, if it is too large, the intramolecular dehydrohalogenation reaction of the starting α,α-dimethylbenzyl halide tends to be enhanced.

Hence, the amount of the catalyst is generally 0.01 to 30 mole %, preferably 0.5 to 10 mole %, especially 1 to 5 mole %, based on the starting α,α-dimethylbenzyl halide or its derivative.

The reaction in accordance with this invention is carried out in a suitable organic solvent. Even in the absence of a solvent, the reaction proceeds by the aid of the catalyst. However, in the absence of solvent, the intramolecular dehydrohalogenation of the starting organic halide occurs markedly, and the final product cannot be obtained in good yields. Suitable organic solvents are aprotic solvents which do not form any salts or adducts with hydrogen halides.

Protic solvents such as water, alcohols, primary or secondary amines, carboxylic acids, sulfonic acid or mercaptan are not used in this invention. Those aprotic solvents which have high reactivity in dehydrohalogenation and form salts or adducts with hydrogen halides, such as dialkyl formamides (e.g., dimethyl formamide), dialkyl sulfoxides (e.g., dimethyl sulfoxide), pyridine, trialkyl phosphines or trialkyl phosphites, can neither be used in this invention.

The aprotic solvents which do not form salts with hydrogen halides include chlorinated aliphatic or aromatic hydrocarbons, esters, nitriles, nitro compounds, ketones and aliphatic or cyclic ethers.

Specific examples of these aprotic solvents are dichloromethane, chlorobenzene, dichlorobenzene, trichloroethylene, methyl formate, ethyl formate, propyl formate, butyl formate, methyl acetate, ethyl acetate, propyl acetate, butyl acetate, ethyl Cellosolve acetate, butyl Cellosove acetate, 1,2-diacetoxyethane, γ-butyrolactone, phenylacetate, acetonitrile, propionitrile, succinonitrile, benzonitrile, tolunitrile, benzyl cyanide, β-methoxypropionitrile, nitromethane, nitroethane, nitropropane, nitrobenzene, nitrotoluene, acetone, methyl ethyl ketone, diethyl ketone, methyl isobutyl ketone, cyclohexanone, diethyl ether, dipropyl ether, dibutyl ether, tetrahydrofuran, 1,2-dimethoxyethane, ethyl Cellosolve methyl ether, 1,2-diethoxyethane, diethylene glycol dimethyl ether, diethylene glycol diethyl ether, dioxane, and anisole.

Non-polar solvents having a very low solubilizing power for the alkali metal cyanates, such as benzene, toluene and xylene, can also be used effectively.

The reaction in accordance with this invention should be carried out in a substantially anhydrous condition because the presence of water, as stated hereinabove, causes undesirable side reactions such as the hydrolysis of the starting organic halide and reduces the yield of the desired organic isocynate. Of course, a completely anhydrous condition is desirable. However, in actual commercial operations, the starting materials, solvent or catalyst may inevitably contain very small amounts of water. In such a case, too, the amount of water should not exceed 0.5% by weight based on the amount of the entire reaction mixture. Experiment has shown that if the amount of water is larger than 0.5% by weight, the yield of the final product markedly decreases.

The reaction in accordance with this invention proceeds smoothly under relatively mild conditions, for example at a temperature of 0° C. to 150° C. The reaction temperature is chosen according to the type of the solvent or catalyst used. The preferred temperature is 20° C. to 80° C.

It has been found that practical effects, such as a further increase in yield or the termination of the reaction within a shorter period of time, can be obtained by causing a small amount of a promotor to be present in the reaction system of the present invention. Such promotors are amines, especially tertiary amines. Specific examples include trialkyl amines or mono- (or di-)alkyl arylamines such as trimethylamine, triethylamine, tripropylamine, tributylamine, triamylamine, trihexylamine, N-monomethylaniline, N,N-dimethylaniline or N,N-dimethylbenzylamine; pyridine and alkyl pyridines such as picoline or methylethyl pyridine alkyl piperidines such as N-methylpiperidine or N-ethylpiperidine; dialkylpiperazines such as N,N'-dimethylpiperazine or N,N'-diethylpiperazine; and alkyl morpholines such as N-methyl morpholine or N-ethyl morpholine. Of these, pyridine is most preferred.

The amount of the promotor should not exceed 2 moles, and preferably be 0.5 to 2.0 moles, per mole of the catalyst described. If the amount of the promotor exceeds 2 moles, the yield of the desired organic isocyanate rather decreases extremely. This is presumable because the promotor in an amount of less than 2 moles combines with the catalyst to promote the activity of the catalyst, but the excess of the promotor beyond 2 moles is present in the form of a free amine in the reaction system, and markedly enhances the dehydrohalogenation reaction of the starting organic halide.

In view of the background of the prior art, it is indeed surprising that by the process of this invention, the reaction of an α,α-dimethylbenzyl halide, i.e. an organic halide containing a tertiary alkyl halide, with an alkali metal cyanate can give the corresponding α,α-dimethylbenzyl isocyanate.

The following Examples and Comparative Examples illustrate the present invention specifically.

For simplification, the following abbreviations are used in these examples.

CC: α,α-dimethylbenzyl chloride (=cumyl chloride)
CB: α,α-dimethylbenzyl bromide (=cumyl bromide)
CI: α,α-dimethylbenzyl isocyanate (=cumyl isocyanate)
MS: methylstyrene or its oligomer

EXAMPLE 1

Fifty millimoles of CC was added to a mixture consisting of 50 ml of ethyl acetate (solvent), 6.5 g (90 millimoles of NaOCN) of sodium cyanate having a purity of 90% and 0.5 millimoles of zinc chloride (catalyst) and being maintained at 65° C. with stirring. The reaction was performed at this temperature for 1.5 hours. (The molar ratio of CC:NaOCN was 1:1.8, and the amount of the catalyst corresponded to 1 mole % of CC.)

The resulting reaction mixture was analyzed by gas-chromatography to obtain the following yields (based on CC).

CI=90.0%, MS=4.2%

EXAMPLES 2 to 18

The procedure of Example 1 was followed under different reaction conditions, i.e. the CC:NaOCN molar ratio, the type and amount of the catalyst, the type of the solvent, the reaction temperature and the reaction time. In all runs, CI was obtained in good yields.

The reaction conditions and the results obtained are shown in Table I together with the data of Example 1. In the table, the molar ratio of the starting materials means the molar ratio of the alkali metal cyanate to the organic halide; the mole % of the catalyst is based on the starting organic halide; and the molar ratio of the promotor is to the catalyst.

EXAMPLES 19 to 31

In these examples, various promotors were further added to the reaction system. A comparison of cases in Examples 1 to 18 with cases in Examples 19 to 31 (for example, Example 13 with Example 25, or Example 16 with Example 30), when operated under comparable conditions, shows that CI can be obtained in a higher yield in the latter cases in which promotors were added, and equivalent yields can be obtained even when the reaction time is short. Example 31 is an example in which cumyl bromide (CB) was used as the starting organic halide, and potassium cyanate, as the alkali metal cyanate.

The reaction conditions and the results obtained are shown in Table I.

EXAMPLES 32 to 42

In these examples, various ring-substituted derivatives of α,α-dimethylbenzyl chloride were used as the starting organic halide. The reaction conditions and the results obtained are shown in Table II.

For simplicity, the starting organic halides used are shown by numbers in Table II. The chemical nomenclature and structural formulas of these halides are shown below.

EXAMPLE 32, (I)

2-(3,4-dichlorophenyl)-2-chloropropane,

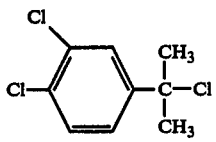

EXAMPLE 33, (II)

p-di(2-chloroisopropyl)benzene,

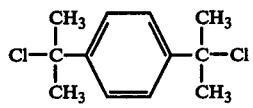

EXAMPLES 34 and 35, (III)

2-(4-fluorophenyl)-2-chloropropane,

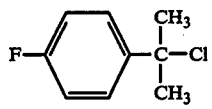

EXAMPLES 36 and 37, (IV)

2-(3-trifluoromethylphenyl)-2-chloro-propane,

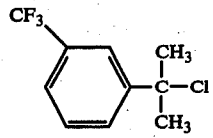

EXAMPLES 38 and 39, (V)

2-(4-methoxyphenyl)-2-chloropropane,

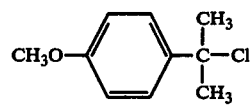

EXAMPLES 40 and 41, (VI)

2-(3-methylphenyl)-2-chloropropane,

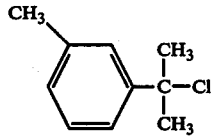

EXAMPLE 42, (VII)

2-(3-chlorophenyl)-2-chloropropane,

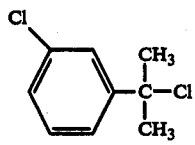

The products were organic isocynates corresponding to the starting organic halides. The product of Example 33 resulted from the conversion of chlorine atoms in the two chloropropyl groups of the starting compound (II) to isocyanate groups. Other symbols in the table have the same meanings as in Table I.

It can be seen from Table II that the use of various ring-substituted cumyl halides as starting materials gives the same good results as does the use of unsubstituted cymyl halides.

COMPARATIVE EXAMPLES (1) TO (20) AND REFERENTIAL EXAMPLE

These examples are comparisons outside the scope of the present invention. The reaction conditions and the results obtained are shown in Table III.

The main differences of the reaction conditions in these examples from the examples of the present invention were as follows:

Comparative Examples (1) to (4): Catalyst was not used.
Comparative Examples (5) and (6): Catalyst was not used, and different solvents were used.
Comparative Examples (7) to (10): Different solvents were used.

Comparative Examples (11) and (12): No solvent was used.
Comparative Example (13): The amount of the promotor was excessive.
Comparative Examples (14) to (20): Water was present in an amount of more than 0.5% by weight in the reaction system.
Referential Example: The example shown in Chem. Abst. Vol. 84, 30650p in which the reaction was performed in the presence of water using N-cetyltrimethylammonium bromide as an inter-phase transferable catalyst.

It will be appreciated from Examples 1 to 42, Comparative Examples (1) to (20) and Referential Example that the process of this invention for producing isocyanates by reacting the corresponding $\alpha,\alpha$-dimethylbenzyl halides or the ring-substituted derivatives thereof with alkali metal cyanates is a novel process which is very advantageous commercially, and that the process is quite unexpected from the prior art.

Table I

| Ex. No. | CC m mol | NaOCN m mol | molar ratio | Catalyst | m mol | mol% | Promotor | m mol | molar ratio | Solvent | ml | Reaction Temp. (°C) | Time (hr.) | Yield Cl (%) | MS (%) |
|---|---|---|---|---|---|---|---|---|---|---|---|---|---|---|---|
| 1 | 50 | 90 | 1.8 | ZnCl₂ | 0.5 | 1 | — | — | — | Ethylacetate | 50 | 65 | 1.5 | 90.0 | 4.2 |
| 2 | " | 100 | 2.0 | ZnSO₄ | 5 | 10 | — | — | — | Acetonitrile | " | room temp. | 7 | 73.4 | 12.3 |
| 3 | " | " | 2.0 | ZnO | 5 | " | — | — | — | " | " | " | 0.6 | 85.2 | 5.2 |
| 4 | 10 | 15 | 1.5 | Zn-acetate | 0.5 | 5 | — | — | — | Ethylacetate | 10 | 50 | 2 | 85.3 | 6.5 |
| 5 | " | 20 | 2.0 | Zn | 1 | 10 | — | — | — | Acetonitrile | a | room temp. | 0.6 | 68.2 | 5.1 |
| 6 | 50 | 100 | " | CoCl₂ | 0.75 | 1.5 | — | — | — | Ethylacetate | 50 | " | 4 | 81.8 | 8.1 |
| 7 | " | " | " | MnCl₂ | 5 | 10 | — | — | — | Acetonitrile | " | " | 5.3 | 77.2 | 6.2 |
| 8 | " | " | " | Pd(NO₃)₂ | " | " | — | — | — | " | " | " | 3 | 80.3 | 11.8 |
| 9 | " | " | " | VCl₄ | " | " | — | — | — | " | " | " | 4 | 86.3 | 6.4 |
| 10 | " | " | " | SnCl₄ | " | " | — | — | — | " | " | " | 0.8 | 85.8 | 3.6 |
| 11 | 10 | 20 | " | Mn | 1 | " | — | — | — | " | 10 | 40 | 3 | 71.9 | 15.9 |
| 12 | 20 | 24 | 1.2 | ZnCl₂ | 0.3 | 1.5 | — | — | — | Ethylacetate | " | 50 | 2 | 91.5 | 4.0 |
| 13 | " | " | " | " | " | " | — | — | — | 1,2-Dimethoxyethane | a | " | 3 | 87.3 | 9.3 |
| 14 | 50 | 90 | 1.8 | " | 2.5 | 5 | — | — | — | Acetone | 50 | " | 1 | 76.7 | 5.1 |
| 15 | " | 53.5 | 1.07 | " | 1 | 2 | — | — | — | Ethylacetate | " | " | 2 | 91.1 | 5.0 |
| 16 | " | 100 | 2.0 | " | 0.25 | 0.5 | — | — | — | " | " | " | 3 | 90.3 | 5.2 |
| 17 | 50 | 100 | 2.0 | ZnCl₂ | 5.0 | 10 | — | — | — | Nitrobenzene | 50 | 70 | 1 | 79.0 | 15.0 |
| 18 | " | 90 | 1.8 | " | " | " | — | — | — | Dioxane | " | 65 | 1 | 86.9 | 10.3 |
| 19 | 10 | 20 | 2.0 | " | 0.2 | 2 | Pyridine | 0.4 | 2.0 | Benzene | 10 | 70 | 1.3 | 91.9 | 7.6 |
| 20 | 50 | 90 | 1.8 | " | 0.5 | 1 | " | 1.0 | " | Ethylacetate | 50 | 50 | 1 | 93.5 | 4.0 |
| 21 | " | " | " | " | 2.5 | 5 | Triethylamine | 5.0 | " | " | " | 65 | 0.4 | 89.4 | 6.6 |
| 22 | " | " | " | " | 0.5 | 1 | N,N-dimethylaniline | 1.0 | " | " | " | " | 1 | 90.5 | 6.4 |
| 23 | " | " | " | " | 0.4 | 0.8 | Pyridine | 0.65 | 1.5 | Dichloromethane | " | 30 | 2 | 93.8 | 2.6 |
| 24 | " | 100 | 2.0 | " | 5.0 | 10 | " | 10 | 2.0 | Chlorobenzene | " | 65 | 0.75 | 82.0 | 5.8 |
| 25 | 20 | 24 | 1.2 | " | 0.3 | 1.5 | " | 0.3 | 1.0 | 1,2-Dimethoxyethane | 10 | 50 | 3.5 | 92.4 | 5.8 |
| 26 | " | " | " | " | " | " | " | 0.5 | 1.7 | Ethylacetate | " | " | 2 | 92.7 | 4.0 |
| 27 | 50 | 90 | 1.8 | " | 5.0 | 10 | " | 10 | 2.0 | Acetone | 50 | " | 0.5 | 73.9 | 5.7 |
| 28 | " | 100 | 2.0 | " | " | " | " | " | " | Nitrobenzene | " | 80 | 0.5 | 77.5 | 17.7 |
| 29 | 250 | 450 | 1.8 | " | 2.5 | 1 | " | 5.0 | " | Ethylacetate | " | 65 | 1.25 | 85.7 | 6.6 |
| 30 | 50 | 90 | " | " | 0.25 | 0.5 | " | 0.5 | " | " | " | " | 1 | 90.8 | 5.6 |
| 31 | CB 50 | KOCN 75 | 1.5 | ZnBr₂ | 5.0 | 10 | " | 10 | " | " | " | " | 3 | 90.3 | 6.2 |

Table II

| Ex. No. | Starting Materials | m mol | NaOCN m mol | molar ratio | Catalyst | m mol | mol% | Promotor | m mol | molar ratio | Solvent | ml | Reaction Temp. (°C) | Time (hr.) | Yield Isocyanate (%) |
|---|---|---|---|---|---|---|---|---|---|---|---|---|---|---|---|
| 32 | I | 30.6 | 61.2 | 2.0 | ZnCl₂ | 3.0 | 9.8 | Pyridine | 6.0 | 2.0 | Ethylacetate | 30 | reflu | 1.5 | 75.5 |
| 33 | II | 41.2 | 165 | 4.0 | " | 2.0 | 4.9 | " | 4.0 | " | Dichloromethane | 60 | room temp. | 5 | 65.6 |
| 34 | III | 77.4 | 154.8 | 2.0 | " | 3.9 | 5.0 | " | 7.8 | " | Ethylacetate | 50 | 60 | 4 | 82.3 |
| 35 | " | " | " | " | " | " | " | — | — | — | " | " | 50 | 5 | 80.6 |
| 36 | IV | 39.2 | 78.4 | " | " | 2.0 | 5.1 | pyridine | 4.0 | 2.0 | Acetonitrile | 40 | 70 | 2.5 | 70.0 |
| 37 | " | " | " | " | " | " | " | — | — | — | " | " | 50 | 4 | 78.4 |
| 38 | V | 45.0 | 90.0 | " | " | 1.0 | 2.2 | Pyridine | 2.0 | 2.0 | Ethylacetate | 50 | 50 | 2 | 86.3 |
| 39 | " | " | " | " | " | " | " | — | — | — | " | " | 50 | 1 | 85.1 |
| 40 | VI | 50.0 | 100 | " | " | 2.5 | 5.0 | Pyridine | 5.0 | 2.0 | " | " | 65 | 0.5 | 91.2 |
| 41 | " | " | " | " | " | " | " | — | — | — | " | " | 50 | 1.5 | 92.3 |
| 42 | VII | " | " | " | " | " | " | Pyridine | 5.0 | 2.0 | " | " | 80 | 4 | 89.3 |

Table III

| Ex. No. | Starting Materials CC m mol | NaOCN m mol | molar ratio | Catalyst m mol | mol% | Promotor m mol | molar ratio |
|---|---|---|---|---|---|---|---|

Table III-continued

| Ex. No. | | | | | | | | | |
|---|---|---|---|---|---|---|---|---|---|
| 1 | 50 | 100 | 2.0 | — | — | — | — | — | — |
| 2 | " | " | " | — | — | — | — | — | — |
| 3 | " | " | " | — | — | — | — | — | — |
| 4 | " | " | " | — | — | — | — | — | — |
| 5 | " | " | " | — | — | — | — | — | — |
| 6 | " | " | " | — | — | — | — | — | — |
| 7 | " | " | " | ZnCl₂ | 1.8 | 3.6 | — | — | — |
| 8 | " | " | " | " | 5.0 | 10 | — | — | — |
| 9 | " | " | " | " | " | " | — | — | — |
| 10 | " | " | " | " | " | " | — | — | — |
| 11 | 100 | 150 | 1.5 | " | 1.0 | 1.0 | — | — | — |
| 12 | 300 | 450 | " | " | 3.0 | 3.0 | Pyridine | 6.0 | 2.0 |
| 13 | 50 | 90 | 1.8 | " | 0.5 | 1.0 | " | 2.0 | 4.0 |
| 14 | 10 | 15 | 1.5 | " | 0.1 | 0.1 | — | — | — |
| 15 | " | " | " | " | " | " | — | — | — |
| 16 | 20 | 30 | " | " | 0.4 | 2.0 | Pyridine | 0.8 | 2.0 |
| 17 | " | " | " | " | " | " | " | " | " |
| 18 | " | " | " | " | " | " | " | " | " |
| 19 | " | " | " | " | " | " | " | " | " |
| 20 | " | " | " | " | " | " | " | " | " |
| Ref. | " | KOCN 20 | 1.0 | CTAB | 1.1 | 5.5 | — | | |

| Ex. No. | Solvent | | H₂O | | Reacton Temp (°C) | Time (hr) | Yield CI (%) | MS (%) | |
|---|---|---|---|---|---|---|---|---|---|
| | | ml | ml | wt% | | | | | |
| 1 | Benzene | 50 | — | | 50 | 1 | 0 | 5 | |
| 2 | Chlorobenzene | " | — | | 80 | 1 | 0 | 8 | |
| 3 | Ethylacetate | " | — | | 50 | 1 | 0 | 4 | |
| 4 | Acetonitrile | " | — | | reflux | 4 | 0 | 98 | |
| 5 | DMF | " | — | | 95 | 5 | 0 | 97 | |
| 6 | DMSO | " | — | | 50 | 1 | 0 | 98 | |
| 7 | DMF | " | — | | 110 | 1.5 | 6.9 | 90 | |
| 11 8 | DMF | " | — | | room temp. | 3 | 10 | 87 | |
| 9 | DMSO | " | — | | 65 | 2 | 0 | 97 | |
| 10 | DMSO | " | — | | room temp. | 3.5 | <5 | 91 | |
| 11 | — | | — | | 50 | 2 | 0 | 27 | |
| 12 | — | | — | | " | 1 | 3.6 | 21.5 | |
| 13 | Ethylacetate | 50 | — | | 65 | 1 | 68.3 | 28.3 | |
| 14 | Ethylacetate | 10 | 0.21 | 2.03 | 55 | 4 | 63.9 | 11.9* | (24.0) |
| 15 | Benzene | " | " | 2.06 | " | 4 | 51.3 | 11.3* | (37.4) |
| 16 | Ethylacetate | 20 | 1.0 | 4.1 | 50 | 2 | 43.7 | 21.0* | (31.2) |
| 17 | Ethylacetate | 50 | 0.27 | 0.53 | " | 1 | 79.9 | 3.3 | (15.1) |
| 18 | Benzene | " | 1.0 | 1.98 | 70 | 2 | 1.5 | 93.3* | ( 4.1) |
| 19 | Benzene | " | " | " | room temp. | 2 | <1 | 98.3* | (trace) |
| 20 | Benzene | " | 0.27 | 0.53 | 70 | 4 | 63.3 | 18.9* | (16.0) |
| Ref. | Benzene | " | 1.0 | 2.2 | room temp. | | 56 | | |

*Total of MS and unreacted CC; the parenthesized figure—reter to the amount of cumyl alcohol.

What we claim is:

1. A process for preparing α,α-dimethylbenzyl isocyanate or its ring-substituted derivatives of the formula

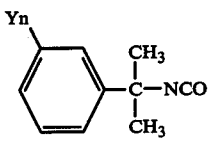

wherein Y is a halogen atom or an alkyl, haloalkyl or alkoxy group each having 1 to 4 carbon atoms and n is an integer of 0, 1 or 2,
which comprises reacting an α,α-dimethylbenzyl halide or its ring-substituted derivative of the formula

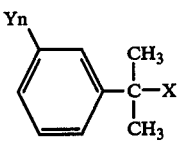

(1)

wherein X is chlorine or bromine, and Y and n are as defined above,
with an alkali metal cyanate in an organic solvent in a substantially anhydrous condition at a temperature of between 0° C. and 150° C. in the presence of, as a catalyst, at least one member selected from the group consisting of metallic V, Mn, Co, Zn, Pd and Sn and oxides and mineral acid salts or carboxylic acid salts of these metals, said organic solvent being an aprotic solvent which forms no salt or adduct with a hydrogen halide.

2. The process of claim 1 wherein the reaction is carried out at a temperature of between 20° C. and 80° C.

3. The process of claim 1 wherein the molar ratio of the starting α,α-dimethylbenzyl halide or its ring-substituted derivative to the alkali metal cyanate ranges from 1:0.8 to 1:4.

4. The process of claim 1 wherein the molar ratio of the starting α,α-dimethylbenzyl halide or its ring-substituted derivative to the alkali metal cyanate ranges from 1:1 to 1:2.

5. The process of claim 1 wherein the reaction is carried out under such a condition that the water content of the starting reaction mixture does not exceed 0.5% by weight.

6. The process of claim 1 wherein the amount of the catalyst ranges from 0.01 to 30 mole % based on the starting α,α-dimethylbenzyl halide or its ring-substituted derivative.

7. The process of claim 1 wherein the amount of the catalyst ranges from 0.5 to 10 mole % based on the starting α,α-dimethylbenzyl halide or its ring-substituted derivative.

8. The process of claim 1 wherein the reaction is carried out in the copresence of at least one promotor selected from the group consisting of trimethylamine, triethylamine, N-monomethylaniline, N,N-diethylaniline, pyridine, picoline, methylethylpyridine, N-methylpiperidine, N-ethylpiperidine, N,N'-dimethylpiperazine, N,N'-diethylpiperazine, N-methylmorpholine and N-ethylmorpholine.

9. The process of claim 8 wherein the amount of the promotor does not exceed 2 moles per mole of the catalyst.

* * * * *